United States Patent
Nicol et al.

(10) Patent No.: US 8,712,514 B2
(45) Date of Patent: Apr. 29, 2014

(54) NEUROPHYSIOLOGICAL CENTRAL AUDITORY PROCESSING EVALUATION SYSTEM AND METHOD

(75) Inventors: Trent Nicol, Chicago, IL (US); Nina Kraus, Evanston, IL (US)

(73) Assignee: Northwestern University, Evanston, IL (US)

( * ) Notice: Subject to any disclaimer, the term of this patent is extended or adjusted under 35 U.S.C. 154(b) by 89 days.

(21) Appl. No.: 13/218,142

(22) Filed: Aug. 25, 2011

(65) Prior Publication Data

US 2011/0313309 A1 Dec. 22, 2011

Related U.S. Application Data

(63) Continuation of application No. 11/382,805, filed on May 11, 2006, now Pat. No. 8,014,853.

(60) Provisional application No. 60/679,751, filed on May 11, 2005.

(51) Int. Cl.
*A61B 5/04* (2006.01)
*A61B 5/00* (2006.01)

(52) U.S. Cl.
USPC .......................................... 600/545; 600/559

(58) Field of Classification Search
USPC .......................................... 600/544, 545, 559
See application file for complete search history.

(56) References Cited

U.S. PATENT DOCUMENTS

2003/0185408 A1* 10/2003 Causevic et al. ............. 381/94.1
2005/0095564 A1* 5/2005 Stuart et al. ................... 434/112

OTHER PUBLICATIONS

Wible. "Correlation between brainstem and cortical auditory processes in normal and language-impaired children". Brain (2005), 128, 417-423 (published Jan. 5, 2005).*
Galbraith et al. "Brainstem Frequency-Following Responses in Rett Syndrome". Pediatric Neurology. 1996;15:25-31.*

* cited by examiner

*Primary Examiner* — Patricia Mallari
*Assistant Examiner* — Christian Jang
(74) *Attorney, Agent, or Firm* — Temmerman Law Office; Mathew J. Temmerman

(57) ABSTRACT

A system and method of central auditory processing testing and evaluation provides for identifying clinically relevant neural synchrony in the auditory brainstem pathway. The system or method finds use as a tool to evaluate auditory processing disorders, and hence, potential auditory system and/or learning disabilities. The system or method may further find use in the selection and fitting of hearing corrective appliances such as hearing aid or cochlear implant devices and/or in the selection and implementation of auditory training regimens.

9 Claims, 2 Drawing Sheets

NEUROPHYSIOLOGICAL CENTRAL AUDITORY PROCESSING EVALUATION SYSTEM AND METHOD

FEDERAL STATEMENT

The U.S. Government has a paid up license in this invention and the right in limited circumstances to require the patent owner to license others on reasonable terms as provided for by the terms of Grant No. ROI-DC01510 awarded by the NIH.

RELATED APPLICATION

This invention was made with government support under grant number R01 DC001510 awarded by the National Institutes of Health. The government has certain rights in the invention.

TECHNICAL FIELD

This patent relates to central auditory processing testing, and more particularly, to a system and method incorporating neurophysiological evaluation of central auditory processing disorders and associated hearing and learning disabilities.

BACKGROUND

Recording the brainstem's response to sound has long been established as a valid and reliable means to assess the integrity of the neural transmission of acoustic stimuli. Transient acoustic events induce a pattern of voltage fluctuations in the brainstem resulting in a familiar waveform that yields information about brainstem nuclei along the ascending central auditory pathway. Accurate stimulus timing in the auditory brainstem is a hallmark of normal perception.

Abnormal perception, understanding and processing of spoken language are fundamental criteria in the diagnosis of many learning disabilities. Currently, central auditory processing disorders are diagnosed through a central auditory processing (CAP) evaluation. Audiologists and speech-language pathologists perform a series of tests, all of which are perceptual and/or audiological in nature, i.e. subjective- not physiological or objective. Auditory brainstem response (ABR) testing provides a physiological indication, but no connection has been established between conventional ABR results and learning disabilities.

Children and adults diagnosed with learning disabilities exhibit highly variable subject profiles. Many factors can contribute to current diagnosis of a learning problem. These include variations in: basic perceptual physiology and higher levels of cognitive function and attention, experientially developed compensatory mechanisms, exposure to previous remedial interventions and differing interpretations of diagnostic categories by clinicians. A consistent and reliable method for diagnosing individuals with learning disabilities has yet to be established.

DETAILED DESCRIPTION

This patent relates to a system and method of central auditory processing testing and evaluation. In accordance with the herein described embodiments, the system and method provide for identifying clinically relevant neural synchrony in the auditory brainstem pathway. A system or method in accordance with the described embodiments finds use as a tool to evaluate auditory processing disorders, and hence, potential auditory system and/or learning disabilities. The system or method may further find use in the selection and fitting of hearing corrective appliances such as hearing aid or cochlear implant devices and/or in the selection and implementation of auditory training regimens.

The system and method utilize a biological marker of auditory processing (or BioMAP), that reflects preconscious aggregate neural activity in the auditory brainstem pathway. The BioMAP exhibits both phasic and tonic encoding, mimicking the acoustic characteristics of the speech signal with high fidelity allowing characterization of normal neural synchrony and subsequent individual evaluation for clinically relevant asynchronous responses. Individual results comparison to a database of normative responses, established from a normal population with high repeatability and low variability, allows the BioMAP to serve as a biological marker for predicting hearing associated disabilities including early detection of childhood learning disabilities.

In one possible implementation, the system and corresponding method of operation of the system is adapted to present a short auditory stimulus to a test subject. Commercially available electrophysiological acquisition technology acquires response data from the subject's brainstem response to the stimulus. Evaluation of the response data using various techniques including statistical analysis and comparison to a database of normative results, provides an objective indication of the presence of central auditory processing disorders.

Figure 1:
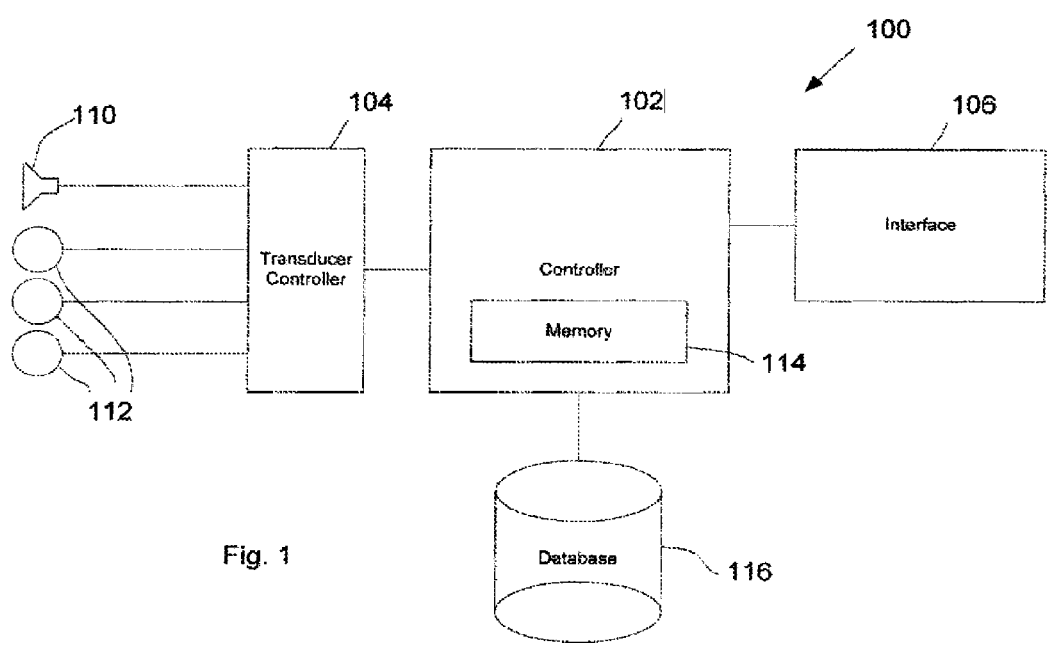
FIG. 1 is a block diagram illustration of a central auditory processing evaluation system.

Referring to FIG. 1, a system 100 includes a processor or controller 102 coupled to a transducer controller 104, a user interface 106 and a database 108. Coupled to the controller 102 via the transducer controller 104 are an audio transducer 110 and a plurality of electrodes 112. While shown as a single element, transducer controller 104 may be separated into elements 104a and 104b. Element 104a may deliver a stimulus to the audio transducer 110, and element 104b may receive and process brainwave signal information from the plurality of electrodes 112. The transducer controller 104 is any suitable stimulus delivery and data acquisition system, including PC-based stimulus delivery and data acquisition systems such as those available from Bio-logic Systems Corporation, Mundelein, Ill. or Compumedics, El Paso, Tex. The audio transducer 110 may be an insert earphone such as the ER-3 insert earphone available from Etymotic research, Elk Grove, Ill. The electrodes 112 may be Ag—AgCl scalp electrodes, which may be positioned on the test subject from Cz (active) to ipsilateral earlobe (reference) with forehead ground.

The controller 102 may be a personal computer (PC) or other suitable general purpose computing device, or may be a dedicated processor. The controller 102 may include memory 114 within which instructions are retained directing the operation of the controller 102 for carrying out the herein described methods and processes. That is, the controller 102 responsive to a control program retained in the memory 114 operates to generate a test stimulus signal, communicates the test stimulus signal to the transducer controller 104 for generation of an audio stimulus that is presented to the test subject via the audio transducer 110. The controller 102 is further operable to obtain brainstem response data via the electrodes 112 and the transducer controller 104. The brainstem response data may be stored within the memory 114, written to the database 116 or presented to a user of the system via the user interface 106. The user interface 106 further permits the user to provide or select instructions and/or parameters for the controller 102 for particular test types, testing parameters and other required data for implementing testing.

The database 116 in addition to including a data structure suitable for storage of acquired brainstem response data, may include one or more data structures used to stored data for analysis of the acquired brainstem response data. For example, the database 116 may contain one or more data structures containing normative response data to which the acquired brainstem response data may be compared to provide comparison data. The database 116 may further contain criteria data for evaluating the comparison data for determining the existence in the test subject of a central processing disorder, auditory disability and/or learning disability. The database 116 may still further contain data permitting the recommendation of remedial measures, such as selection of hearing assistive appliances and/or auditory training regimens.

In one embodiment, a test group having a statistically significant membership is used to develop the normative data retained in the database 116. The members of this group are selected for having no medical or learning difficulties. For example, before acceptance into the test group each member must first meet minimum acceptable criteria on accepted learning and achievement testing as well as on one or more hearing evaluation methodologies, such as, evoked auditory brainstem response (ABR) tests.

In one embodiment, the testing methodology includes developing a stimulus signal that may be transduced to form an audio stimulus for communication to the test subject. The stimulus signal may include a transient peak element and a sustained element. Such a signal is typical of speech, and for example, the stimulus signal may be a multi-formant synthesized speech sound. In one exemplary embodiment, the stimulus signal is a five-formant synthesized Ida! having a 40 millisecond (ms) duration.

The audio stimulus may be presented as a single stimulus or as part of a train of stimuli, monaurally or binaurally, with the same or alternating polarities, at constant or varying sound pressure level (SPL), at constant or variable intervals, and in the presence or absence of noise. The criteria for the presentation of the audio stimulus are dependent on the type of evaluation being performed and the type of disability being screened or identified. The /da/ stimulus may be presented in a stimulus train, monaurally, in alternating polarities, at 80 dB SPL to the right ear via an insert earphone, with an inter-stimulus interval of 51 ms. A sound source is also provided to the non-test ear at less than 40 dB SPL. The stimulus train may consist of train segments wherein the stimuli within a segment have an inter-segment interval, measured in milliseconds, and the train segments have an inter-train interval, also measured in milliseconds. For example, the 40 ms /da/ stimulus may be presented in segments of four stimuli separated by an inter-stimulus interval, e.g., 10 ms, with each segment being separated by an inter-train interval, e.g., 30 ms.

Figure 2:
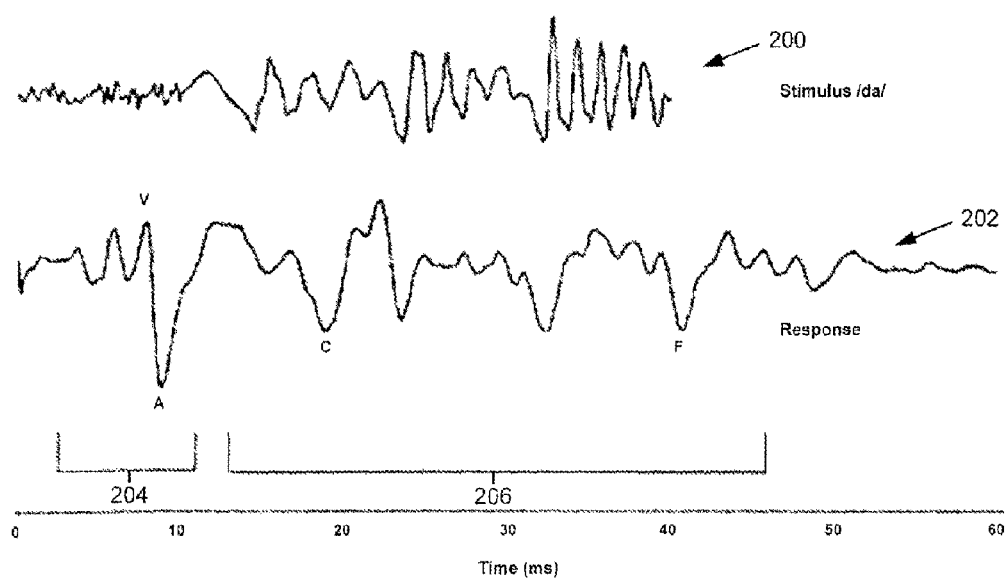
FIG. 2 is a graph depicting a stimulus signal and a resulting evoked brainstem response.

Typically a large number of stimuli are presented and corresponding results recorded and combined into an average waveform. One example of collecting and determining the average waveform may be recording the results as a number of representative files, averaging the data, and plotting the data as an average waveform. The stimuli may be presented as three sets of 1000 events in opposite polarities. For example, the stimulus may be presented a total of 6000 times, 3000 times each for each polarity, with a cycle of 1000 stimulus events. The results may be presented as a number of files of the recorded results as presented to the subject in one polarity, each file including a complete stimulus cycle. For example, a test involving 6000 stimulus presentations may result in 6 separate data result files. The data of the resulting files may then be combined to achieve an average waveform. With reference to FIG. 2, an example of the resulting average waveform may be illustrated by 202.

The electrophysiological brainstem response to a speech sound may be represented as a complex waveform 202. The brainstem response to the /da/ stimulus consists of a number of major peaks. The number of peaks considered may be decreased or increased without a loss of test accuracy. For example, peaks may be examined from merely the waveform's onset portion 204, the frequency following response (FFR) portion 206, or a combination of either or both portions. With reference to FIG. 2, any combination of peaks V, A, C and F may be reliable response measurements. FIG. 2 illustrates the stimulus waveform 200 for the stimulus /da/ and the resulting average brainstem response waveform 202, averaged from brainstem response data obtained from thirty-eight test subjects. The waveform 202 illustrates transient peaks making up the onset portion 204 as well as sustained elements making up the FFR portion 206. The onset of the speech stimulus /da/ response includes a positive peak (V) followed immediately by a negative trough (A). Following the onset 204 or transient response, peaks C and F are present in the FFR portion 206. Additional peaks are also visible. It is therefore possible to determine, on a normative basis, the latency and amplitude of each peak for various stimuli, both in quiet and in noise environments.

In addition to the latency and amplitude of the individual peaks, e.g., V, A, C and F, relationships within the data may be determined and analyzed. For example, inter-peak intervals, amplitude, slope and area are measurable. Statistical relationships also may be established. Characteristics of the onset portion 204 (e.g., the VA inter-peak slope and the VA inter-peak area) as well as characteristics of the FFR portion 206 (e.g., amplitude determined using root-mean-square (RMS), Fourier transform or other suitable special analysis techniques, stimulus-to-response correlation, and quiet-to-noise inter-response correlation) may be measured.

All of these data when gathered from subjectively determined normal test subjects are indicative of normal brainstem response to the subject stimulus. Moreover, research demonstrates that speech-evoked brainstem response faithfully reflects many acoustic properties of the speech signal. In normally-perceiving auditory systems, stimulus timing, on the order of fractions of milliseconds, is accurately, precisely and repeatably represented at the level of the brainstem. Thus, these normative data associated with normal response characteristics when stored as part of the database 116 provide a tool for comparison of brainstem response data from a test subject as part of a hearing and/or learning disability or more generally a central processing disorder evaluation system and method.

In operation of the system 100 as a tool for hearing and/or learning disability evaluation, responsive to a user instruction received via the interface 106, the controller 102 initiates a test as herein described. It should be noted that the system 100 may be capable of conducting any number of hearing tests, such as, evoked auditory brainstem response (ABR), otoacoustic emission (OAE) and the like in addition to the herein described protocols. Thus, the system 100 may be a robust device for the evaluation and diagnosis of various hearing-related disorders.

The test may consist of presentation of an acoustic stimulus, e.g., the /da/ stimulus; acquiring brainstem response data from the test subject responsive to the acoustic stimulus;

analyzing the brainstem response data to identify response characteristic data; comparing the response characteristic data to a set of normative data to provide comparison data; and determining an existence of a central processing disorder based upon the comparison data.

In that regard, the control program retained in the memory 114, or otherwise provided to the controller 102, may include at least one data processing routine. The control program may include three data processing routines. The first routine achieves extraction from the response characteristic data from the brainstem response. That is, the first routine identifies the position of a number of the peaks (e.g., peaks V, A, C and F) in the brainstem response data and records characterizing information regarding the peaks. The characterizing information may include root mean square (RMS) analysis, Fast Fourier Transform (FFT) analysis, and cross-correlation calculations. The results of these calculations may then be saved to the database 116 to be compared and analyzed in routine two. One example of suitable algorithms for these calculations may be supplied by MATLAB® as produced by The Mathworks, Inc. of Natick, Mass.

The test may optionally include an analysis of subject response in the presence of background noise. The background noise may be in the form of stimuli other than the /da/ that may cause a brainstem response. With background noise, the data may be modified to allow more efficient extraction and identification of the peaks. For example, the data may go through a De-Noising Routine. One example of an effective De-Noising Routine may be based on Wavelet Decomposition or any other suitable method such as those described in "De-Noising by Wavelet Transform" by Qian, "On wavelet analysis of auditory evoked potentials" by Bradley et al., or "Single-trial event-related potentials with wavelet de-noising" by Quiroga, et al.

For the first routine, characteristics of the onset portion 204 (e.g., the VA inter-peak slope and the VA inter-peak area) as well as the FFR portion 206 (e.g., amplitude determined using root-mean-square (RMS), a measurement of spectral content representation in the brainstem response using a Fast Fourier Transform or other suitable techniques, stimulus-to-response correlation, and quiet-to-noise interresponse correlation) may be measured.

In the onset portion 204, the VA inter-peak slope may be a measure of the onset timing, and may be defined as the change in amplitude with respect time. One example of the VA inter-peak slope may be calculated as follows:

$$\text{Slope} = (\text{VA complex amplitude})(\text{VA complex duration}) =$$
$$(\text{peak } A \text{ amp} - \text{peak } V\text{amp}) / (\text{peak } A \text{ latency} - \text{peak } V \text{ latency}).$$

Also in the onset portion, the VA inter-peak area is a measure of the onset magnitude. One example of the VA inter-peak area may be calculated as follows:
1) subtract wave A amplitude from the amplitude of every point between wave V and wave A, and
2) sum the resulting amplitudes of all points between peaks in V and A.

In the FFR portion 206, RMS is a measure of the magnitude and may be calculated as the square root oft he mean of the squares of the amplitude. One example of calculating the RMS may be as follows:
Step 1: Create a baseline FFR, normalized such that the mean is zero;
Step 2: Square the amplitudes of each point in the FFR;
Step 3: Sum the results of step 2;
Step 4: Divide the result of step 3 by the total number of selected points in the FFR; and Step 5: Take the square root of the result of step 4.

A Fast Fourier Transform (FFT) may be used to obtain the spectral components of the sustained portion of the response that correspond to the stimulus fundamental frequency (Fo amplitude), the frequencies of the first formant of the stimulus (F1 amplitude), and the frequencies of the higher frequencies of the stimulus (HF). F0 amplitude, F1 amplitude, and HF amplitude may be measures of how well the spectral component of the stimulus is represented in the brain stem response. The baselined FFR region may be windowed with a 2 ms on –2 ms off Hanning ramp. To increase the spectral estimate, the windowed FFR region may be padded with zeros (to the length n, where n is the number of samples in 1 second) before taking the FFT. F0 amplitude may be calculated as the absolute value of the FFT amplitude across the range of fundamental frequencies. F1 amplitude may be calculated as the average of the absolute values of the FFT amplitudes across the first formant frequencies. HF may be calculated as the average of the absolute values of the FFT amplitudes across the second and third formant frequencies. Fo amplitude, F1 amplitude, and HF amplitude values may also be evaluated with respect to the presence of those frequencies in the non-stimulus-evoked neural activity.

Also in the FFR portion 206, the Stimulus-to-Response correlation may be a measure of how well the timing features of the stimulus waveform are preserved in the response. The correlation may also be a measure of how well the response phase locks to the stimulus. To account for the time it takes for the acoustic stimulus to travel through the nervous system (approximately 7 to 11 ms), a static portion of the 2000 Hz low-pass filtered version of the stimulus that includes the harmonic segment may be cross-correlated with a portion of the response. A series of crosscorrelations may be performed, with a lag between the stimulus and response increasing incrementally with each successive correlation. Two Pearson's correlation coefficients (r-value) may then be reported: 1) the maximum positive r-value in the 8 to 10 ms lag range and the maximum negative r-value in the 7 to 9 ms lag range.

A Quiet-to-Noise Inter-Response Correlation may also be measured. Background noise may introduce a delay in the brainstem response compared to the response in quiet. The delay may be on the order of 0 to 2 ms, and may be found by finding the maximum Pearson's correlation coefficient in a series of correlations between a static portion of the quiet response corresponding to the FFR period, and an equivalently long portion of the noise file. With each successive correlation, the noise response may be shifted later in time.

A second routine provides for clinical review of the characteristic data with respect to the normative data stored in the database 116. Furthermore, complex associations within the data, such as inter-peak intervals, amplitude, slope and area as well as statistical relationships and characteristics of the FFR portion 206 may be considered. A score may be established based on the first routine calculations that may contribute to the clinical review. The score may be called a BioMAP score and consist of the normative values of five ABR measures including, in the onset portion 204: 1) wave V latency; 2) wave A latency; 3) VA slope; and in the FFR portion 206: 4) the average energy of the measured first formant frequencies (F1); and 5) the average energy of the high frequencies (HF).

For each of the five measures, a standard score or z-score for each measure may be calculated. The quantity z represents the number of standard deviations between the raw score and the mean; it is negative when the raw score is below the mean, positive when above. The z-scores may allow easier comparison across the different measures. Further, each z-score may be modified so that each may be easier to compare. For example, for each of the wave V latency, wave A latency, and VA slope, larger z-score values may be more abnormal. However, the opposite may be true for the average energy of the measured first formant frequencies and the average energy of the high frequencies. The negative z-scores may then be multiplied by −1 so that the z-scores may more easily be compared.

Each z-score may then be assigned a value depending on the z-score value. For example, a z-score greater than 2 may be assigned a value of 4, a z-score greater than 1.5, but less than 2 may be assigned a value of 2, a z-score greater than 1, but less than 1.5 may be assigned a value of 1, and any z-score less than 1 may be assigned a value of 0. The assigned values may then be added together to achieve an intermediate score.

However, because the five measures were converted to standard scores, it may be possible to achieve identical intermediate scores despite having very different measurements. For example, a subject having an abnormal measurement in the onset phase 204 may achieve an identical intermediate score as another subject having an abnormal measurement in the FFR phase 206 despite the fact that abnormal measurements in the onset phase 204 are a stronger indication of a subject's abnormality than similar measurements during FFR 206. Therefore, the five measures may be analyzed to determine which variables discriminate between normal and abnormal subjects. The differences between the five measures may be taken into account using a discriminant function to determine a predictor of group membership, or a group predictor (X). An example of a discriminant function may be as follows:

X=(a×Wave V Latency)+(b×Wave A Latency)+(c×VA Slope)+(d×F1)+(e×HF)+k Where a, b, c, d, and e are coefficient values that may define the relationship of each of the five measures, and k is a constant value. The constant value may be added to ensure that the group predictor will be either above 0 or below 0. The coefficients and the constant may be found using analytical data mining software such as SPSS® as produced by SPSS, Inc. of Chicago, Ill. If the group predictor is below 0, the subject is predicted to be abnormal and a value of 1 may be added to the intermediate score. If the group predictor is above 0, the subject is predicted to be normal and a value of 1 may be subtracted from the intermediate score. The combination of the intermediate score and the group predictor may be a final composite score, or the BioMAP score. This may result in a range of possible values from 0 to 22.

The data resulting from scoring (i.e., the final composite score) may then be processed by a third routine in a manner that allows determination of presence of a central auditory processing disability, and particularly, a central auditory processing associated learning disability. The determination may include comparison of the BioMAP score against a range of BioMAP scores indicating a delineation between normal and abnormal subjects. For example, a BioMAP score within a specific range (i.e., 5 to 22) may indicate a central processing disorder in the subject, while a lower score (i.e., 0 to 4) may indicate the absence of a central processing disorder.

In the example described, the system 100 finds application in the determination of a central auditory processing disability, and particularly an associated learning disability. The system 100 and methods may find further application with the selection and fitting of hearing assistive appliances such as hearing aids and/or cochlear implants. That is, comparison of the characteristic data with normative data allows for the identification of specific hearing related disorders. Selection of a hearing assistive appliance or alternatively an auditory training regime is custom selectable for the individual.

The invention has been described in terms of several embodiments, including a number of features and functions. Not all features and functions are required for every embodiment of the invention. The features discussed herein are intended to be illustrative of those features that may be implemented; however, such features should not be considered exhaustive of all possible features that may be implemented in a device configured in accordance with the embodiments of the invention. Moreover, the herein described embodiments are illustrative and not limiting of the invention. The invention is defined and limited only by the following claims.

We claim:

1. A system comprising:
a controller coupled to a database including normative data, the controller including an associated memory including a control program, having one or more data processing routines configured to extract brainstem response data from a brainstem response and store it in a database;
a transducer controller coupled to the controller, the transducer controller operable to generate an acoustic stimulus response to a stimulus signal received from the controller and to acquire brainstem response data from the brainstem response;
a transducer coupled to the transducer controller to transduce the acoustic stimulus to provide an audible signal, and to present the audible signal to the test subject;
a plurality of electrodes configured to detect the brainstem response within the test subject as a result of the presentation of the acoustic stimulus and to communicate the brainstem response to the transducer controller;
wherein the acoustic stimulus comprises a signal having a transient peak element and a sustain element;
wherein the one or more data processing routines is configured to process the extracted brainstem response data stored in the database to provide a clinical review of the response characteristic with respect to normative data stored in the database; and
wherein the one or more data processing routines is configured to generate a composite score based on combination of one or more intermediate scores and one or more group predictors to determine the presence of auditory processing disability.

2. The system of claim 1, the brainstem response data comprising an onset response portion including a data peak portion having a peak magnitude and a data trough portion having a trough magnitude.

3. The system of claim 1, the brainstem response data comprising a frequency following portion including a data trough portion having a trough magnitude.

4. The system of claim 1, wherein the controller is configured to compare a characteristic of a peak data portion of the brainstem response data to the normative data.

5. The system of claim 1, wherein the controller is configured to compare a characteristic of a trough data portion of the brainstem response data to the normative data.

6. The system of claim 1, wherein the central auditory processing disorder comprises a preconscious, disordered processing of sound stimulus.

7. The system of claim 1, wherein the central auditory processing disorder is associated with a learning disability.

8. The system of claim 1, the controller is configured to recommend a remedial measure in view of the central processing disorder.

9. The system of claim 8, wherein the remedial measure comprises at least one of a hearing assistive appliance or an auditory training regimen.

\* \* \* \* \*